United States Patent [19]
De Hollander et al.

[11] Patent Number: 5,763,230
[45] Date of Patent: Jun. 9, 1998

[54] AMINO ACID FERMENTATION PROCESSES

[75] Inventors: J. A. De Hollander, NE Oegstgeest; F. R. Eswilder, WJ Delft; J. A. C. Noordover, CP Pijnacker, all of Netherlands

[73] Assignee: Triple-A B.V. p/a Produkschap voor Veevoedor, Netherlands

[21] Appl. No.: 710,199

[22] Filed: Sep. 13, 1996

[30] Foreign Application Priority Data

Mar. 22, 1996 [EP] European Pat. Off. ............ 96200797

[51] Int. Cl.$^6$ .................... C12P 13/04; C12P 13/08; C12P 13/14
[52] U.S. Cl. .................... 435/106; 435/110; 435/115
[58] Field of Search .................... 435/106, 110, 435/115

[56] References Cited

U.S. PATENT DOCUMENTS

| | | | |
|---|---|---|---|
| 4,400,467 | 8/1983 | Bauer et al. | 435/104 |
| 4,411,991 | 10/1983 | Hirakawa et al. | 435/42 |
| 4,480,034 | 10/1984 | Shieh | 435/136 |
| 4,833,078 | 5/1989 | Hsieh | 435/142 |
| 5,498,532 | 3/1996 | Katsumata et al. | 435/106 |

FOREIGN PATENT DOCUMENTS

| | | |
|---|---|---|
| 0199499 | 10/1986 | European Pat. Off. . |
| 2331614 | 6/1977 | France . |
| 285991 | 5/1989 | German Dem. Rep. . |

OTHER PUBLICATIONS

Chen, H.C. Food Biotechnology, vol. 7 (3), pp. 221–234, Abstract Enclosed, 1993.

*Primary Examiner*—Leon B. Lankford, Jr.
*Assistant Examiner*—Christopher R. Tate
*Attorney, Agent, or Firm*—Bierman, Muserlian and Lucas

[57] ABSTRACT

The present invention relates to a process for the fermentative production of an amino acid which comprises the use of phosphorous limited or phosphorous/carbon double limited growth conditions during the fermentative production.

6 Claims, 6 Drawing Sheets

AMINO ACID FERMENTATION PROCESSES

The present invention relate to industrial amino acid fermentation processes.

Amino acids, such as glutamic acid, lysine, threonine, and others, are commercially produced in fermentation processes, often employing species from the Corynebacterium genus or closely related bacteria. Such fermentation processes are usually of the batch type or of the fed-batch type. In batch type fermentations all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time. Prolonging a fermentation in this way has a significant positive effect on the over-all fermenter productivity (average amount of product formed per hour), because the influence on productivity of the turn-around time (the period between two successive runs) is diminished. Although described in the scientific literature for amino acids fermentations, the long term continuous fermentation principle is not known to be used in practice for the commercial fermentative production of amino acids. There are several reasons for the apparent absence of utilization of the continuous fermentation technique on industrial scale. One of the main reasons is the phenomenon of culture degeneration. Amino acids are normally produced using genetically improved microorganisms, which have been selected for a higher yield of the amino acid of interest. Such improved organisms generally loose the growth competition with their parental counterparts. Reversion of improved strains to a lesser producing variant is a common problem during long term cultivation, and under competitive conditions this will lead to a loss in culture productivity after some time.

In a batch fermentation an organism grows until one of the essential nutrients in the medium becomes exhausted, or until fermentation conditions become unfavourable (e.g. the pH decreases to a value inhibitory for microbial growth). In fed-batch fermentations measures are normally taken to maintain favourable growth conditions, e.g. by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous. The latter two types of limitation are less common employed, because most organisms require only small amounts of these compounds for growth, and it can be difficult to achieve such a limitation during an industrial scale fermentation, especially when raw materials of a complex or partly unknown composition are used. In a continuous culture the yield of biomass (the biomass concentration in the culture fluid which is ultimately obtained, at steady state) is dependent on the concentration of the growth limiting nutrient in the feed medium. When this concentration is increased, maintaining other nutrients at the same concentration level, the biomass concentration in the culture increases until one of the other nutrients becomes limiting. A further increase of the concentration of the original limiting nutrient leads to the accumulation of this compound in the culture, without a further increase in biomass yield. In such a procedure of stepwise increasing the conciantrallon of a limiting nutrient, it is possible to arrive at a condition of double limitation, characterized by the (almost) complete utilization of two different nutrients. This condition of double limitation is very poorly studied at present.

The present invention concerns the use of a fermentation regime leading to phosphorous flmitation or preferably to combined phosphorous and carbon limitation, applied in fed-batch or continuous culture systems. It was found that the use of such conditions during an Industrial scale fermentation leads to remarkable and surprising improvements of the fermentation performance in several aspects.

The application of a condition of phosphate limitation or preferably a condition of phosphorotis-carbon double limitation is found to have several advantages. For all mentioned aspects, the most optimal condition is a condition close to the transition from unitary phosphorous limitation to phosphorous-carbon double limitation. Under phosphorous limitation accumulation of valuable carbon source In the medium will occur. This is economically less attractive, because a part of the raw materials remains unused. There might also be an environmental disadvantage, because the culture fluid after separation of the amino acid will still have a considerable COD (chemical oxygen demand). According to tho present process the steady state (or pseudo-steady state in fed-batch culture) is just phosphorous limited, with only a slight accumulation of residual sugar, or just in the region of carbon-phosphorous double limitation with both limiting nutrients practically exhausted. Advantacgeously the present Invention resulted in an improved yield of product on consumed carbon source.

On a molasses-based medium an improvement in yield of lysine on consumed carbon source was obtained: 0.4 g lysine.HCl per g glucose was found under phosphorous/carbon double limitation, as compared with 0.375 g lysine-.HCl per g glucose found under carbon source limitation (an improvement of 6.6%).

We also found that the present process resulted in an improved fermenter productivity.

The productivity of a certain fermentation equipment is normally maximized by supplying carbon source at such a rate that the oxygen consumption rate just matches the oxygen transfer capacity of the equipment. Supplying carbon source at a higher rate will lead to oxygen limitation or to a drop in the dissolved oxygen concentration to a level unfavourable for amino acid production. The oxygen transfer capacity is determined by the rheological properties of the fermentation fluid, and mainly by the available agitation power and the maximum back pressure which can be applied. When back pressure and/or agitation power are increased by technological measures, cooling of the fermenter content can become limiting. In aerobic processes the heat production is determined by the amount of power input via stirring and aeration, and the production of metabolic heat. The latter is known to be proportional to the rate of oxygen consumption of the process. For either situation, a limited oxygen transfer capacity, or a limited cooling capacity, the over-all yield of product on oxygen directly determines the maximum productivity of the fermentation equipment. A simple formula can express this relationship: productivity (kg product per $m^3$ per hour)=oxygen transfer capacity (Mol $O_2$ per $m^3$ per hour)×yield on oxygen (kg product per Mol $O_2$). For a lysine producing fermentation under carbon limitation an average yield on oxygen of 0.0255 kg lysine.HCl per Mol $O_2$ as found. Using optimal phosphorous/carbon double limited conditions a yield on oxygen of about 0.030 kg lysin.HCl per Mol $O_2$ was found. For a typical oxygen transfer capacity of a conventional fermentation vessel or 125 Mol $O_2$ per $m^3$ per hour maximum productivities of 3.18 kg Lysine.HCl per $m^3$ per hour under carbon limitation and 3.75 kg Lysine.HCl per $m^3$ per hour for phosphorous/carbon double limitation were obtained, an improvement of 17% for phosphorous/carbon double limitation in comparison with carbon limitation.

A general phenomenon in long term continuous fermentation of genetically improved strains is degeneration of the culture productivity after some time. With a lysine producing *Corynebacteriufi glutamicum* strain it was invariably found that after 300 to 400 hours continuous cultivation at a dilution rate of 0.05 $h^{-1}$ (20 to 30 generations) the culture productivity suddenly drops to a low value. Surprisingly, under phosphorous limitation and under phosphate/carbon double limitation this phenomenon did not occur (see Example 2). It is easy to calculate the effect on the average culture productivity resulting from the prolongation of fermentation time, tor instance from 300 hours to 1000 hours. The productivity is proportional to the ratio of the effective production period ($T_p$) to the total duration of the fermentation, which is the effective production period plus the duration of the non-productive batch phase ($T_b$), plus the time needed for cleaning, refilling and sterilization of the ferrtientation for the next run ($T_o$). The productivity is proportional to $T_p/(T_p+T_b+T_o)$. For $T_b=24$ and $T_o=24$ a productivity improvement of 10% is obtained when the effective production time increases from 300 hours to 1000 hours.

Biomass production is an Inevitable by-product of an amino acid fermentation. It is often difficult to find a suitable and economic outlet for this by-product. One of the advantages of the use of phosphorous limitation or phosphorous-carbon double limitation is a great reduction in biomass production. This is also advantageous for the down stream processing of the fermentation broth, as the biomass separation step will require less washing water to obtain a desired yield. In FIG. 1 it can be seen that the steady state biomass concentration drops sharply when phosphorous becomes (co-)limiting. The lysine concentration remains at approximately the same level up to the point where unitary phosphorous limitation starts. This means that the specific rate of lysine production ($q_p$ g Lysine.HCl per gram biomass per hour) shows a very significant increase. Under carbon limitation the $q_p$ for the test strain was about 0.084 gram Lysine.HCl per gram biomass (dry weight) per hour when the continuous fermentation was run at a dilution rate of 0.07 $h^{-1}$. Under phosphorous limitation or phosphorous/carbon double limitation the $q_p$ was 0.24 gram Lysine.HCl per gram biomass (dry weight) per hour, using the same dilution rate. In practice this means that for the same amount of lysine produced 65% less biomass is formed under optimal phosphorous/carbon double limitation conditions.

LEGENDS TO THE FIGURES

Figure 3:
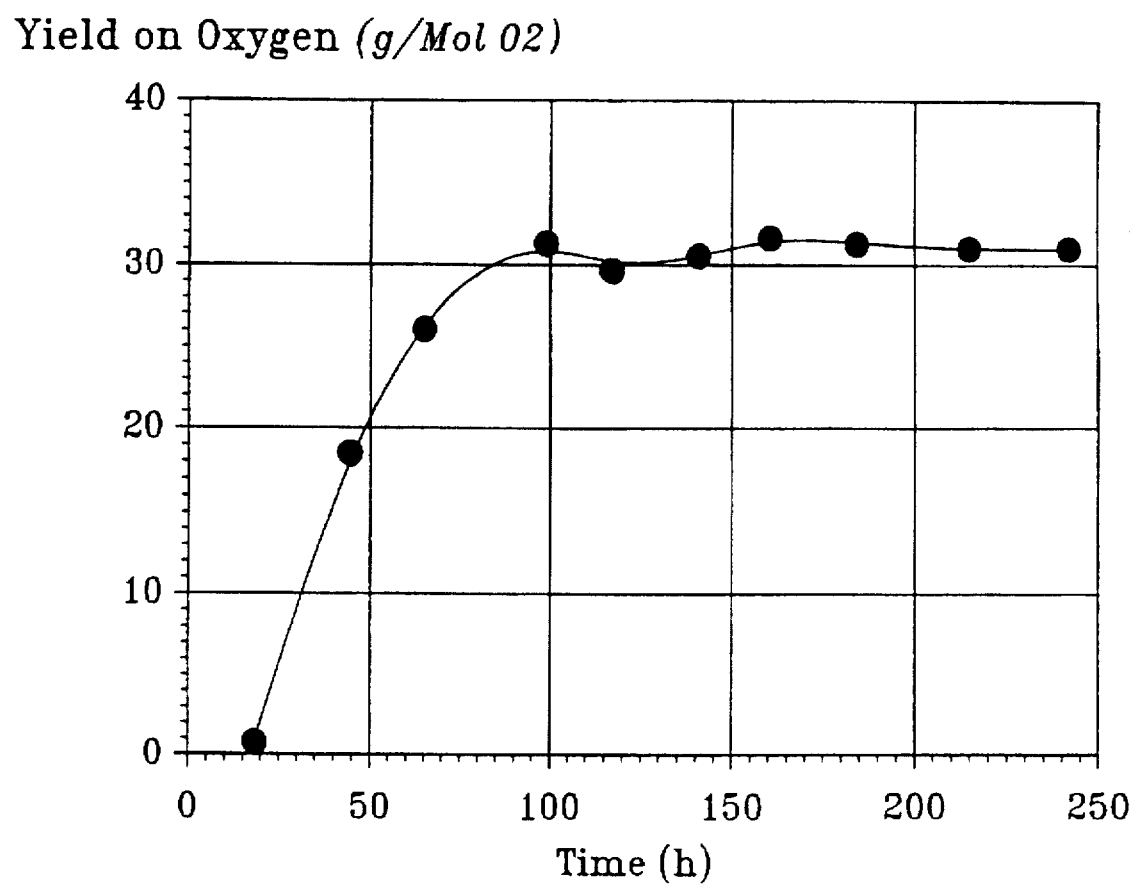

FIG. 3 shows the yield of Lysine.HCl on consumed oxygen as a function of time, for a typical continuous fermentation: dilution rato 0.07 $h^{-1}$, carbon source concentration of the feed medium 150 g/glucose equivalents, oxygen uptake rate 125 Mol/$m^3$/h.

Figure 4:
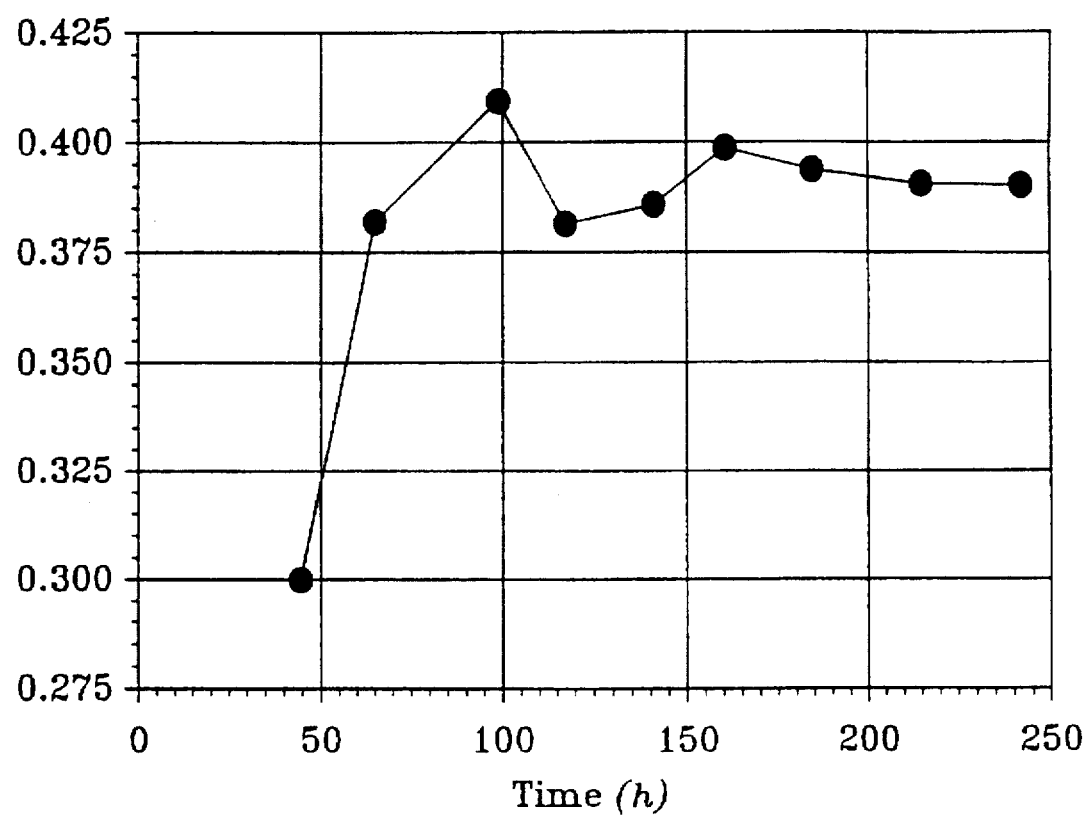

FIG. 4 shows the yield of Lysine.HCl on consumed carbon source for the same fermentation as in FIG. 3.

Figure 5:
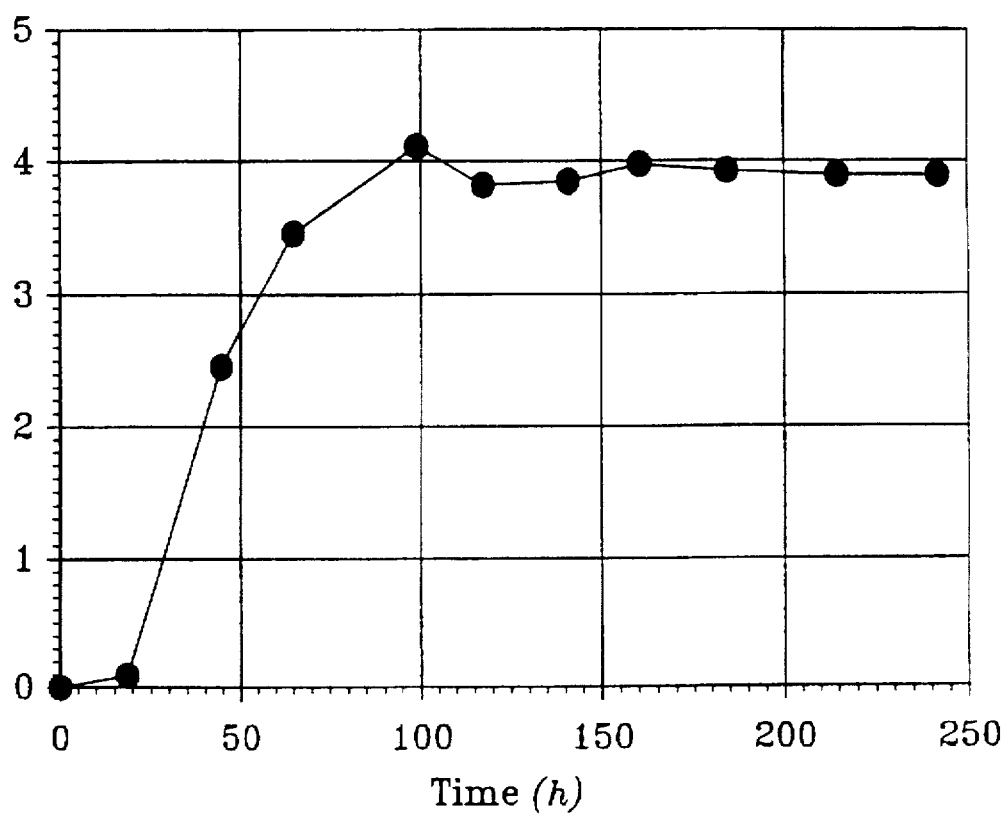

FIG. 5 shows the momentary productivity of the same fermentation as in FIG. 3 and FIG. 4.

Figure 6:
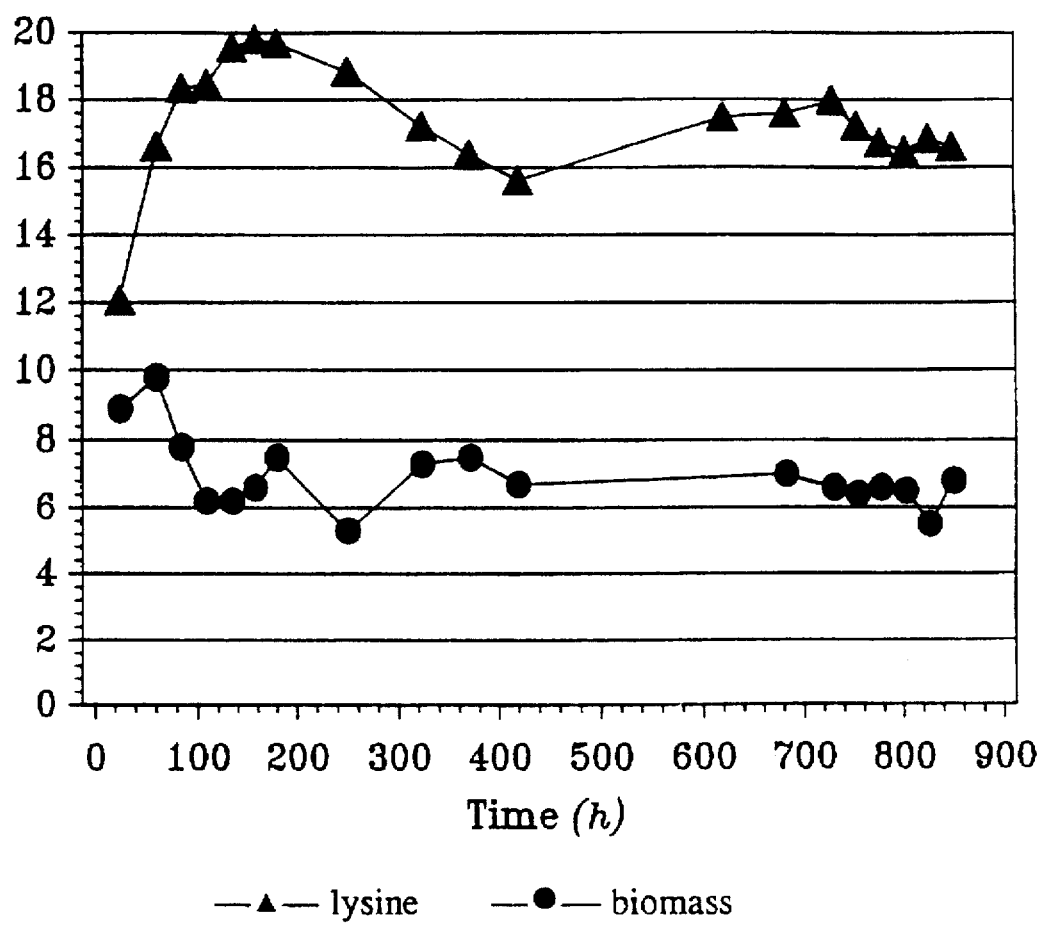

FIG. 6 shows the lysina and biomass concentrations in a phosphorous/carbon double limited continuous culture. The culture did run for nearly 900 hours at a dilution rate of 0.07 $h^{-1}$ using a feed medium containing 50 g/glucose equivalents.

EXAMPLE 1

In the following a possible protocol is described to establish a long term stable and highly productive fermentation for the production of lysine on a medium based on beet molasses, suitable for a fermentation equipment with a maximum oxygen transfer capacity of 125 Mol per $m^3$ per hour, using a dilution rate of 0.07 $h^{-1}$. The protocol can easily be adapted for other fermentation equipments or for the production of other amino acids using a similar microorganism. When other raw materials than molasses are used, the phosphate content of that raw material should be checked. Beet molasses contain insignificant amounts of available phosphorous. Low amounts of phosphorous in the raw material are tolerable, but the described doses of phosphate should be adjusted. Such an adjustment is also necessary when the producing organism has a phosphorous content deviating from the test organism, which had a phosphate content of 0.363 mMol per gram dry weight under phosphorous-limited conditions When other dilution rates are used, the concentration of carbon source described in the protocol should be adjusted inverse proportional to the dilution rate, in order to reach the desired oxygen uptake rate of 125 Mol per $m^3$ per hour.

1. Preparation of the Inoculum

An inoculum culture is prepared in a shake flask of 500 ml, containing 100 ml of medium suitable for growth of the organism. The shake flask Is inoculated with a small amount of the microorganism taken from an agar slant or another suitable storage form of the strain. When the working Volume of the continuous culture is in the order of 10 liters the shake flask culture, grown in a rotary shaker to the stationary phase, can be used directly to inoculate this fermentation. For larger volumes one or more subsequent inoculation phases of increasing volume will be used.

2. Batch Phase Medium

The continuous fermentation is started as a batch fermentation. The fermenter is filled with a medium of the following composition; beet molasses diluted with water up to a sugar concentration of 50 gram per kg; per kg medium is added: $(NH_4)_2SO_4$ 5 g; $KH_2PO_4$ 0.225 g; $MgSO_4 7H_2O$ 2 g; $FeSO_4 7H_2O$ 75 mg; $CuSO_4 5H_2O$ 1 mg; $ZnSO_4 7H_2O$ 1.5 mg; Citric acid 0.5 g; Ca-D-pantothenate 30 mg; Thiamine-.HCl 15 mg; Biotin 0.7 mg; Nicotinic acid 40 mg.

3. Feed Media

Beet molasses is diluted up to a sugar concentration of 150 gram per kg. Tho same additions per kg medium are done as for the batch phase medium. Potassium-dihydrogenphosphate however is now added to an amount of 0.54 gram per kg medium.

A second feed is prepared composed of 85% phosphoric acid (8.76 Mol phosphorous per kg).

4. Start-up Phase of the Continuous Culture

The batch medium is inoculated with the inoculum culture. The culture will grow exponentially until the carbon source is exhausted, as indicated by a sharp drop in oxygen uptake rate. At that time (after 15 to 20 hours, depending on the inoculum size and viability) feeding of molasses medium and phosphoric acid is started at a rate of ⅓ of the final rates. After 12 hours of feeding the teed rates are increased to ⅔ of the final rates. After 24 hours of feeding the feed rates are set at their final value. Continuous withdrawing of fermentation fluid starts as soon as the working volume of the fermenter is reached, and is set at such a flow rate that the volume of the culture fluid in the fermenter remains constant.

5. The Continuous Phase

The two feeds (diluted molasses medium and phosphoric acid) are set at flow ratio's of 8750:1. The total flow is 70 kg per m³ working volume per hour, resulting in a dilution rate of 0.07. For instance, for a vessel of 100 litres working volume this will result in a molasses medium flow rate of 7 kg per hour. and a phosphoric acid flow rate of 0.8 g per hour. The carbon source will be limiting from the start of the feeding phase. Phosphorous will become (additionally) limiting within 24 hours after the start of feeding. Normally the culture will need some time for adaptation to the condition of phosphoroustcarbon double limitation, which may result in initial biomass concentrations which are slightly higher than in steady state.

6. Control of the pH and the Ammonia Concentration

Both biomass growth and lysine production results in acidification of the medium. This must be compensate by the addition of some base titrant. When pH control at the set-point of 6.8 is done using a mixture of ammonia and ammonium sulphate in a 1:0.8 ratio (based on equimolar nitrogen contents of the two titrants), the addition of $NH_4^+$ will approximately match the use of ammonia for growth and lysine production The set-point for ammonia level control is 1 g per litre. Small deviations may occur during the fermentation, which can be corrected by adding a suitable amount of ammonium sulphate in case the ammonia level is too low, or by temporary switching to sodium carbonate or another nitrogen-free base titrant for pH control in case the ammonia concentration becomes too high.

7. Control of Oxygen Transfer Rate

The fermentation will be run at an oxygen transfer rate close to the maximum oxygen transfer capacity of the fermentation system. Variations of the predicted oxygen transfer rate may occur due to small variations in the medium feed rate or the carbon source concentration in the feed. When the deviation in oxygen uptake rate exceeds a tolerance level, a simple control action in activated, which changes both feed rates and the withdrawal rate in proportion to the deviation of the oxygen uptake rate from the desired value (when the oxygen uptake rate is too low, the flow rates are increased).

8. Control of the Degree of Phosphorous Limitation

Optimum productivity is obtained when the culture is at the transition point from phosphorous limitation to phosphorous-carbon double limitation. It may be necessary to change the preset ratio of flow rates, for instance due to small variations in the actual concentration of either the carbon source or the phosphate/phosphoric acid. A change in the flow rate of the phosphoric acid feed is used to change the phosphorous/carbon ratio of the combined feeds without a significant effect on the dilution rate. Accumulation of carbon source in the culture fluid is an indication of insufficient phosphorous feeding. The phosphoric acid flow rate should be increased when a critical level is exceeded. The degree of phosphorous limitation in the region of phosphorous/carbon double limitation can be monitored via the concentration of biomass (dry weight). When this concentration exceeds a pre-set value, the flow of phosphoric acid should be decreased.

EXAMPLE 2

Figure 1:
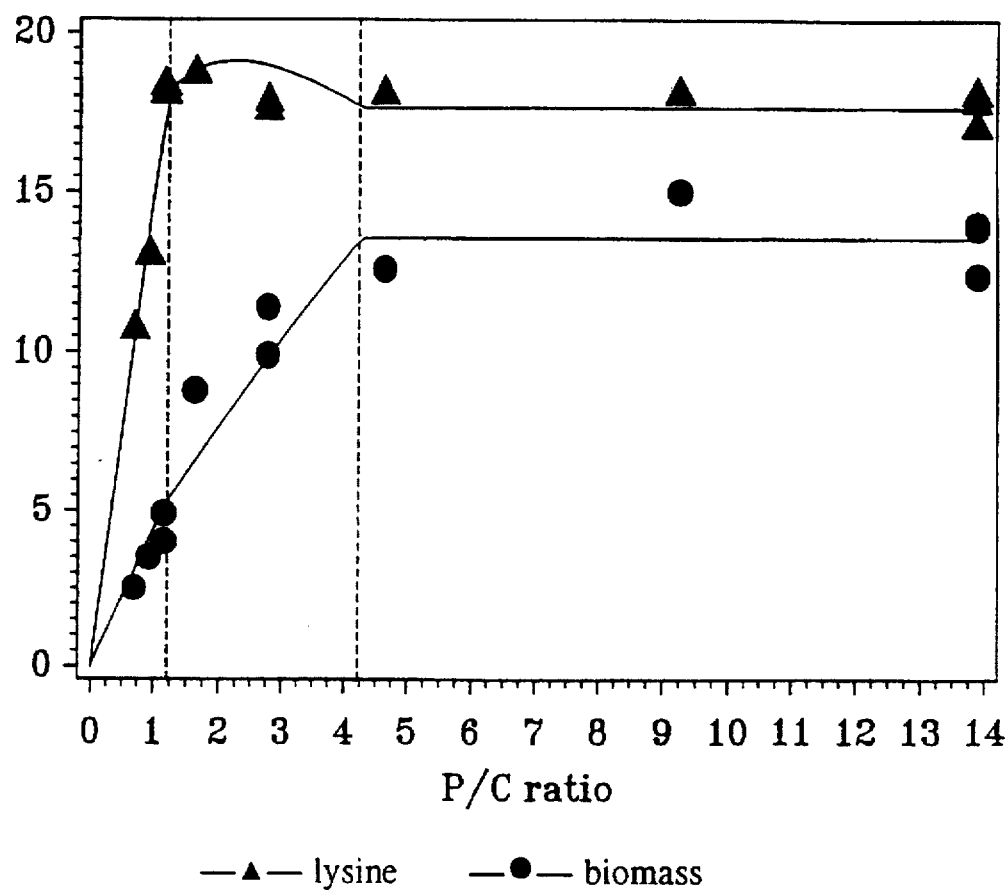
FIG. 1 shows the concentration of lysine and biomass in the culture fluid as a function of the phosphorous/carbon ratio (P/C ratio) In the feed medium for a series of continuous fermentations all using a medium containing 50 g/l glucose equivalents. The P/C ratio is expressed as mMol phosphorous per Mol consumable carbon.
Figure 2:
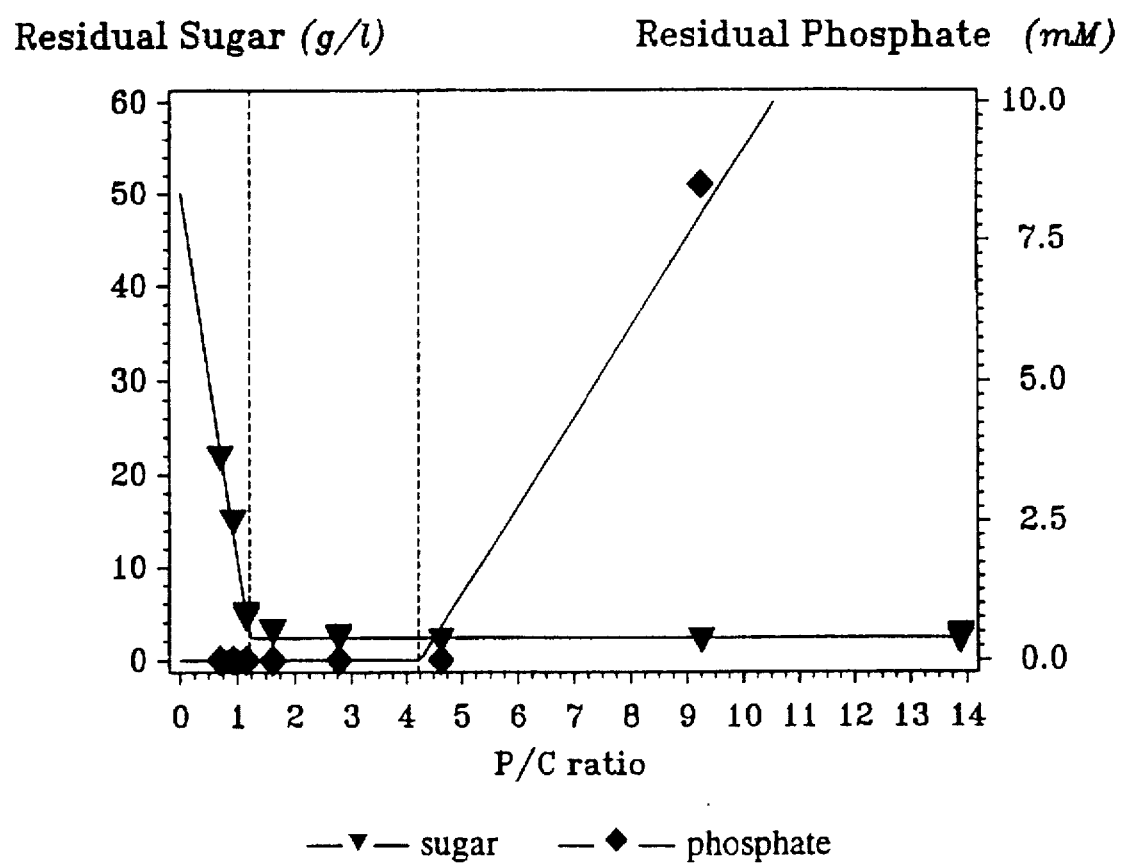
FIG. 2 shows the concentration of sugar and phosphate in the culture fluid for the same series of fermentations as in FIG. 1.

A lysine over-producing *Corynebacterium glutamicum* strain was tested in continuous culture, using different ratios of phosphorous and carbon in the food medium. A diluted beet molasses medium was supplemented with vitamins and minerals, and varying amounts of potassium-di-hydrogen phosphate. Sugar was determined by the reducing sugar method. A sugar concentration of 50 g/l was used in these experiments. FIG. 1 show the, concentrations of lysine. (as lysine.HCl) and biomass (as dry weight) in the culture fluid as a function of the phosphiorous/carbon ratio in the feed medium. At low phosphate concentrations In the medium a condition of phosphorous limitation results; at high phosphate concentrations the culture becomes carbon-limited, There appeared to exist an intermnediate region of phosphorous-carbon double limitation. In the present example the optimal phosphorous/carbon ratio was 1:1 mmol phosphorous per mol of consummable carbon. In general the optimal phosphorous/carbon ratio will be between 0.5 to 4.0 mmol phosphorous per mol of consummable carbon depending on the microorgaism used and raw materials used. The transition points between phosphorous limitation, phosphorous/carbon double limitation, and carbon limitation are indicated in FIGS. 1 and 2 by vertical dashed lines. FIG. 2 shows tho concentration of sugar and phosphate in the culture fluid. In FIG. 1 shows that the relative concentrations of lysine and blomass in the culture are strongly dependent on the degree of s phosphorous limitation, with a maximum around the transition from phosphorous limitation to phosphorous-carbon double limitation.

EXAMPLE 3

A process as described above was carried out in a 10 liter fermentation vessel. A steady-state oxygen uptake rate of 126 mMol per liter per hour was obtained. FIG. 3 shows the yield of lysine on oxygen. FIG. 4 shows the yield of lysine on consumed carbon source. FIG. 5 displays the actual (momentary) productivity of the fermentation system per unit broth volume, as a function of the fermentation time. In steady state a productivity of about 3.8 kg lysine.HCl per m³ per hours was obtained.

EXAMPLE 4

A process as described, but with a more diluted medium of 50 g glucose per kg, was cared out in a 1.5 liter fermentation vessel and was run for 850 hours without any sign of culture degeneration (FIG. 6).

We claim:

1. In a process for the fermentative production of an amino acid in a culture medium to which a growth feed medium is added, the improvement comprises the use of phosphorus and carbon limited growth conditions in the culture medium during the fermentative production, whereby said growth feed medium is composed to give said phosphorous and carbon limited growth conditions, whereby the phosphorous/carbon ratio in the growth feed medium is between 0.5 to 4.0 mMol of phosphorus per Mol of consumable carbon.

2. The process of claim 1 wherein the amino acid is selected from the group consisting of glutamic acid, lysine and threonine.

3. The process of claim 1 wherein the growth feed medium is continuously added.

4. The process of claim 1 wherein the growth feed medium is discontinuously added.

5. The process of claim 1 wherein the fermentation is effected for at least 100 hours.

6. The process of claim 1 wherein the amino acid is isolated.

* * * * *